(12) United States Patent
Ikuta et al.

(10) Patent No.: US 10,912,468 B2
(45) Date of Patent: Feb. 9, 2021

(54) PULSE MEASURING DEVICE, PULSE MEASURING UNIT, AND ELECTRONIC APPARATUS

(71) Applicant: SONY CORPORATION, Tokyo (JP)

(72) Inventors: Tomoya Ikuta, Kanagawa (JP); Atsushi Ito, Kanagawa (JP)

(73) Assignee: SONY CORPORATION, Tokyo (JP)

(*) Notice: Subject to any disclaimer, the term of this patent is extended or adjusted under 35 U.S.C. 154(b) by 295 days.

(21) Appl. No.: 15/777,870

(22) PCT Filed: Nov. 16, 2016

(86) PCT No.: PCT/JP2016/083913
§ 371 (c)(1),
(2) Date: May 21, 2018

(87) PCT Pub. No.: WO2017/098872
PCT Pub. Date: Jun. 15, 2017

(65) Prior Publication Data
US 2018/0368709 A1 Dec. 27, 2018

(30) Foreign Application Priority Data

Dec. 7, 2015 (JP) .................................. 2015-238185

(51) Int. Cl.
*A61B 5/024* (2006.01)
*A61B 5/00* (2006.01)
*A61B 5/0245* (2006.01)

(52) U.S. Cl.
CPC ...... *A61B 5/02427* (2013.01); *A61B 5/02438* (2013.01); *A61B 5/681* (2013.01); *A61B 5/0245* (2013.01); *A61B 2562/0238* (2013.01)

(58) Field of Classification Search
CPC . A61B 5/02427; A61B 5/681; A61B 5/02438; A61B 5/0245; A61B 2562/0238
(Continued)

(56) References Cited

U.S. PATENT DOCUMENTS 5,913,819 A * 6/1999 Taylor ................ A61B 5/14552
29/832
8,320,985 B2 * 11/2012 Miller ................ A61B 5/14551
600/324

(Continued)

FOREIGN PATENT DOCUMENTS

| CN | 1479864 A | 3/2004 |
|---|---|---|
| CN | 1736331 A | 2/2006 |

(Continued)

OTHER PUBLICATIONS

International Search Report and Written Opinion of PCT Application No. PCT/JP2016/083913, dated Jan. 31, 2017, 10 pages of ISRWO.

*Primary Examiner* — Jacqueline Cheng
*Assistant Examiner* — Tho Q Tran
(74) *Attorney, Agent, or Firm* — Chip Law Group

(57) ABSTRACT

A pulse measuring device of the disclosure includes a housing, a light-emitting device, a light-receiving device, and a light guide body having a first end surface facing the light-emitting device, a second end surface facing the first end surface and facing the light-receiving device, one or a plurality of first side surfaces covered by the housing, and one or a plurality of second side surfaces exposed from the housing.

11 Claims, 12 Drawing Sheets

(58) Field of Classification Search
USPC .......................................................... 600/502
See application file for complete search history.

(56) References Cited

U.S. PATENT DOCUMENTS

| | | |
|---|---|---|
| 2004/0024541 A1 | 2/2004 | Uchida et al. |
| 2006/0041195 A1 | 2/2006 | Shioi et al. |
| 2010/0217098 A1 | 8/2010 | Leboeuf et al. |
| 2017/0079591 A1* | 3/2017 | Gruhlke ............... A61B 5/6898 |

FOREIGN PATENT DOCUMENTS

| | | |
|---|---|---|
| EP | 1422512 A1 | 5/2004 |
| EP | 1627596 A1 | 2/2006 |
| JP | 07-184883 A | 7/1995 |
| JP | 2001-296244 A | 10/2001 |
| JP | 2006-081893 A | 3/2006 |
| JP | 2012-518515 A | 8/2012 |
| JP | 2012-176225 A | 9/2012 |
| JP | 2015-093163 A | 5/2015 |
| WO | 03/021239 A1 | 3/2003 |
| WO | 2003/021239 A1 | 3/2003 |

* cited by examiner

[FIG. 1]
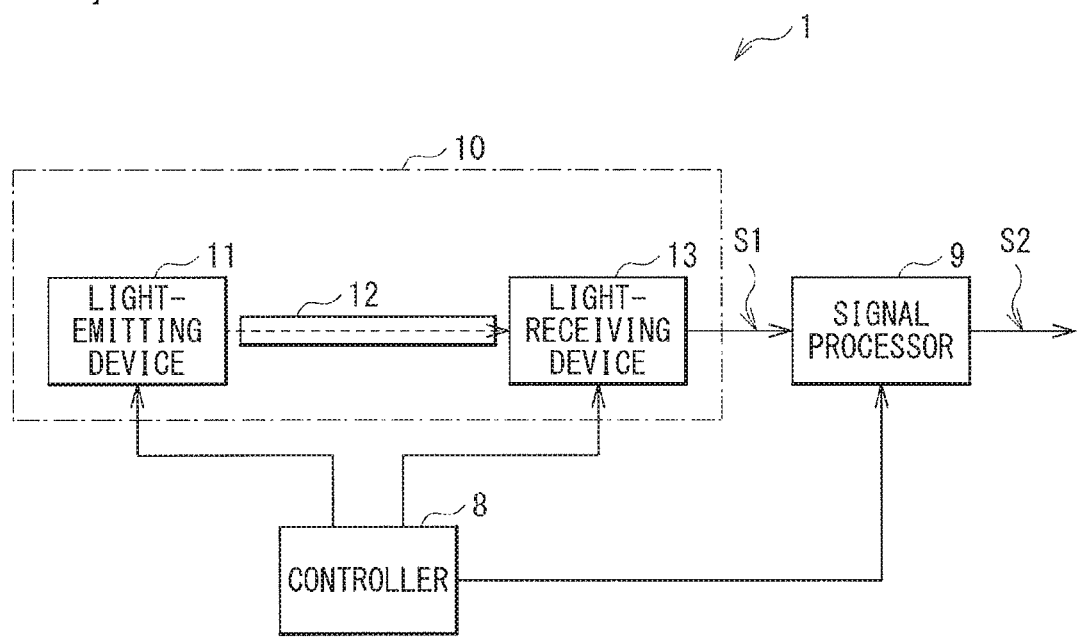

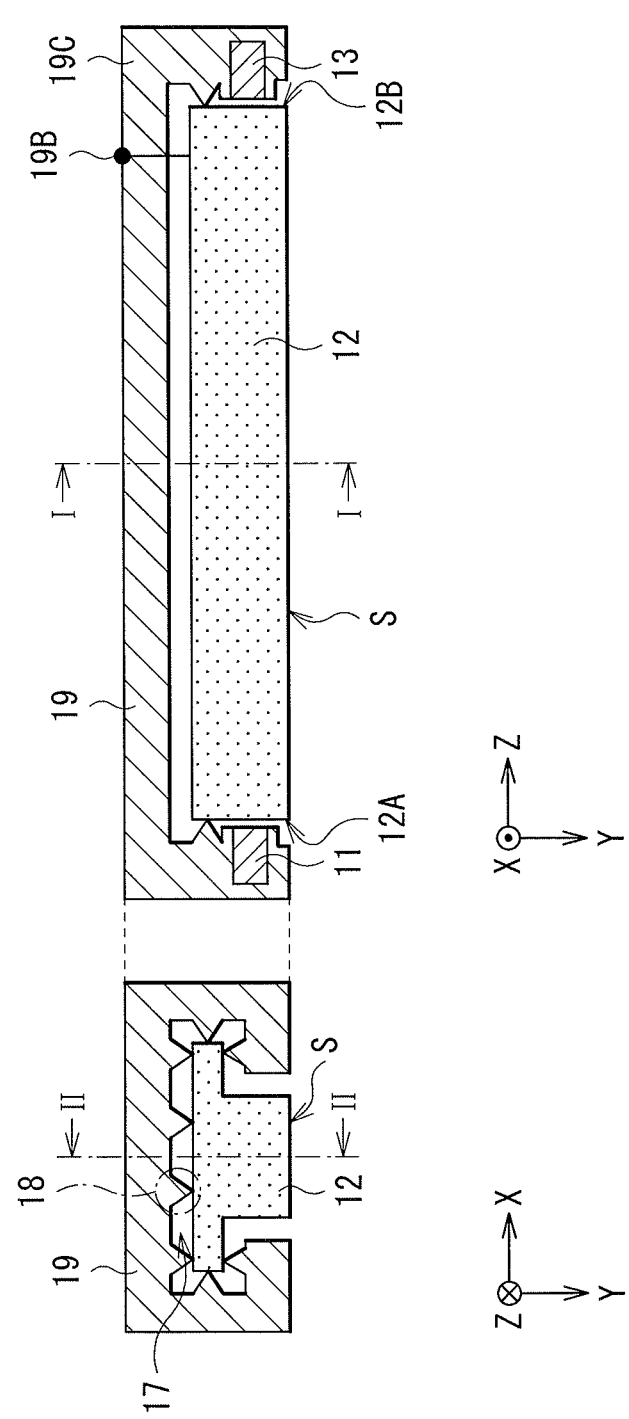

[FIG. 3]
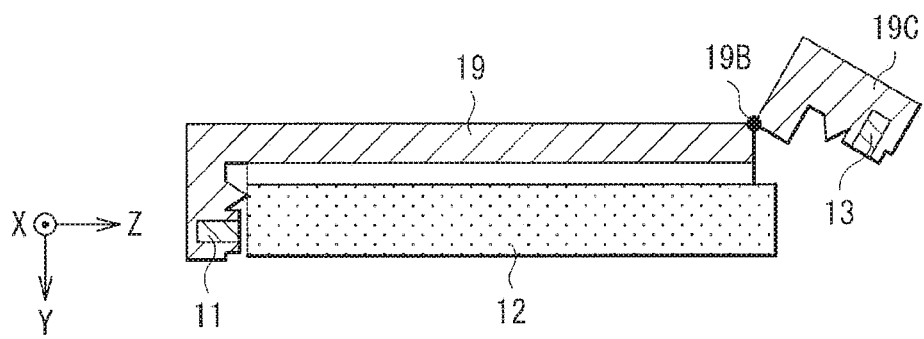
[FIG. 4A]
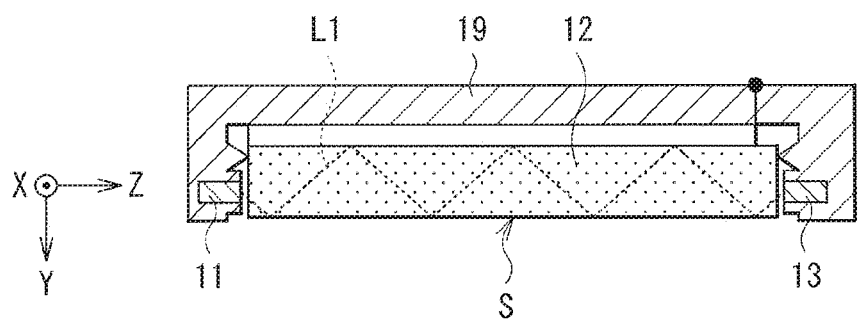
[FIG. 4B]
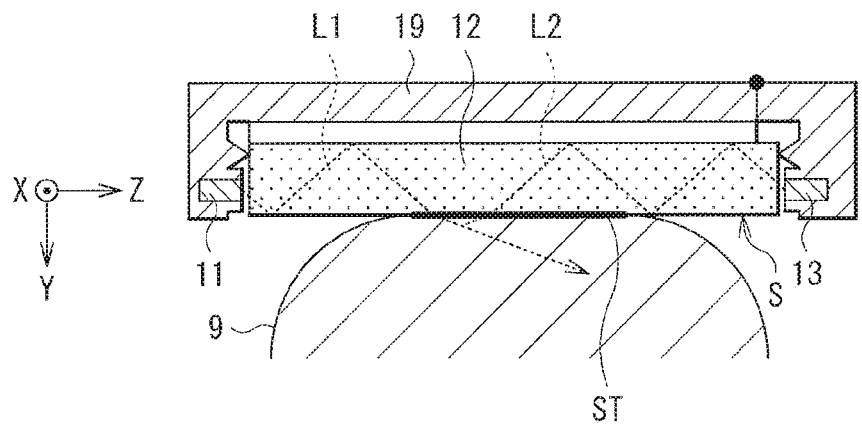

[ FIG. 5 ]
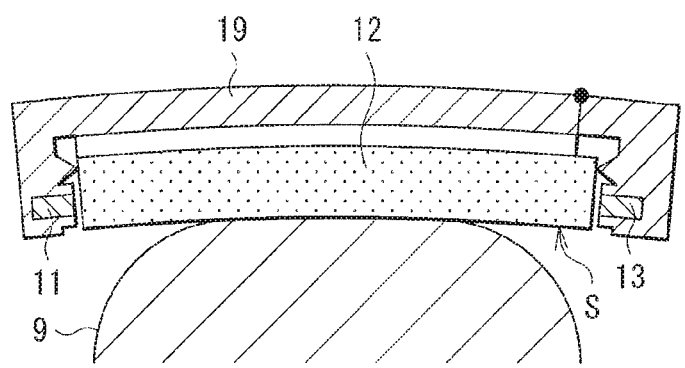
[ FIG. 6 ]
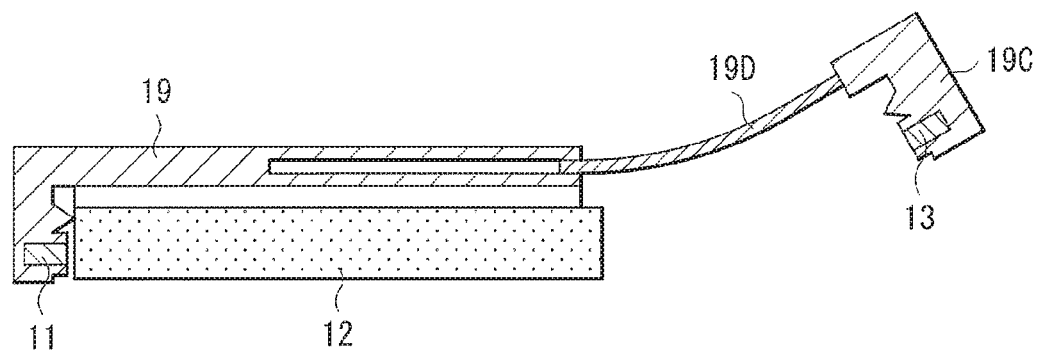

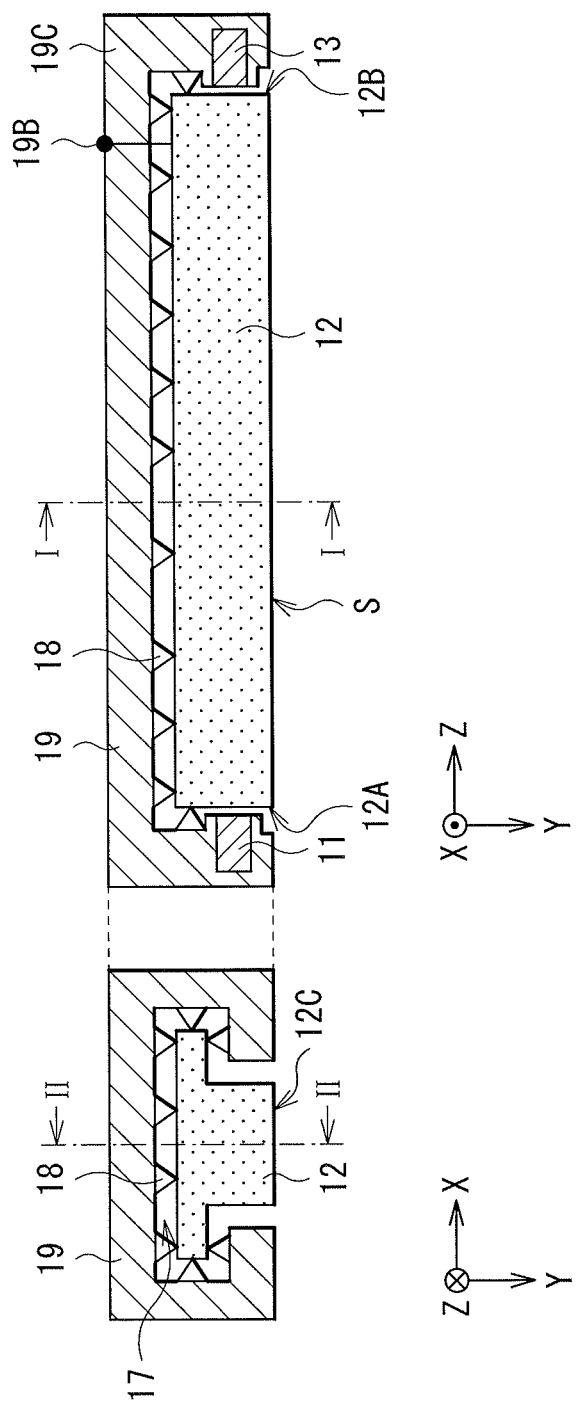

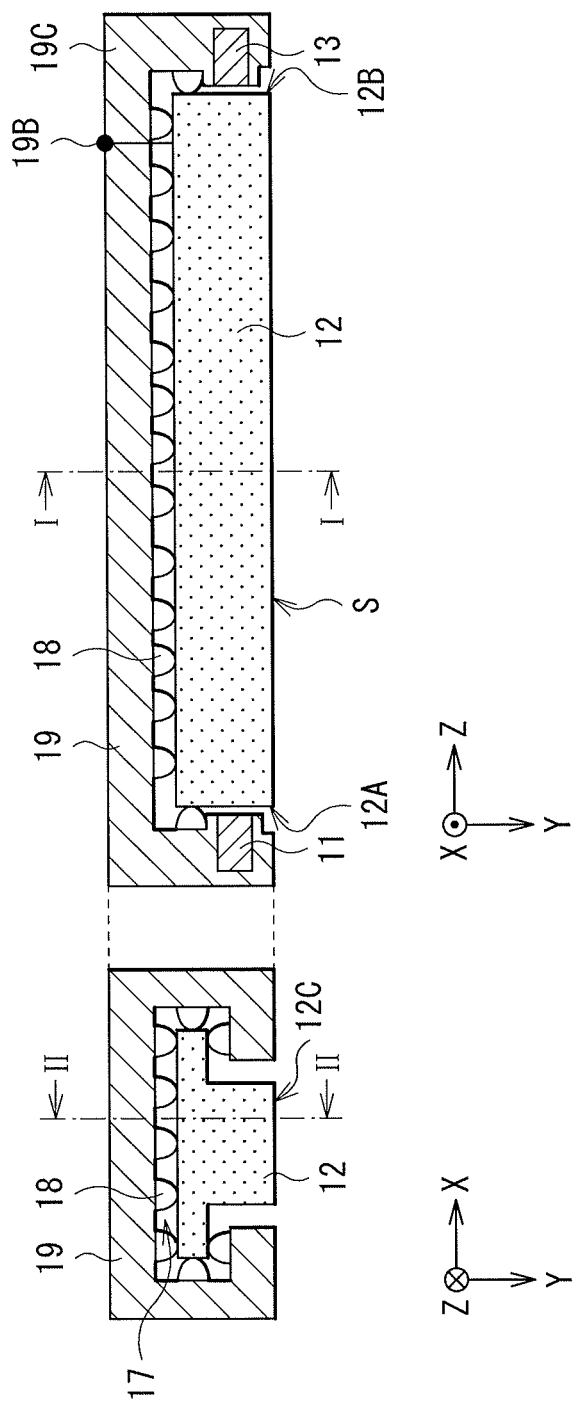

[ FIG. 9A ]
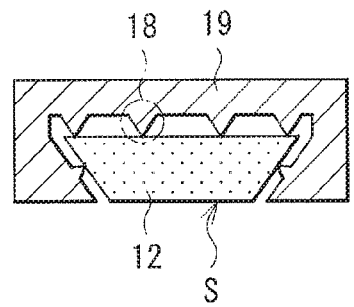
[ FIG. 9B ]
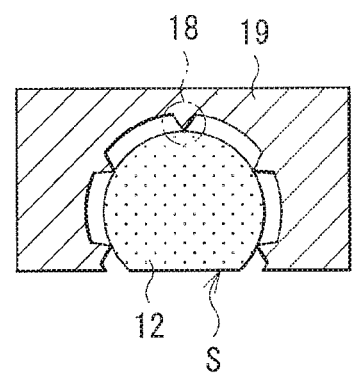
[ FIG. 9C ]
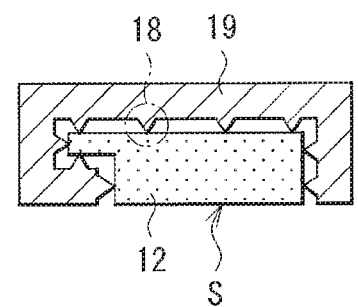
[ FIG. 9D ]
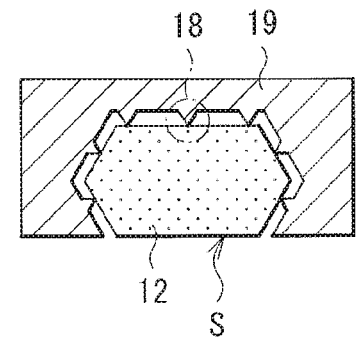

[ FIG. 9E ]
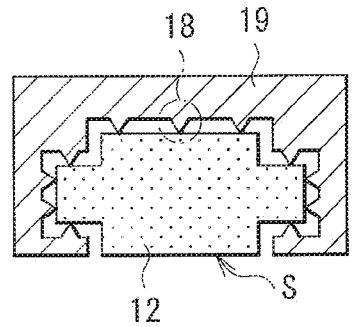
[ FIG. 9F ]
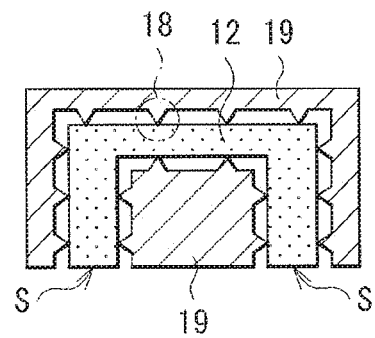
[ FIG. 9G ]
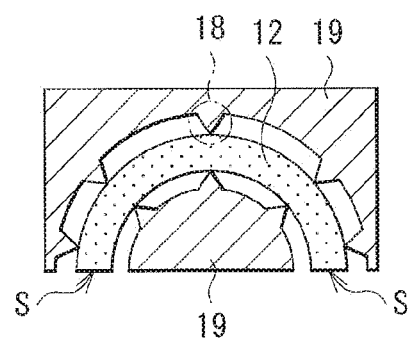
[ FIG. 9H ]
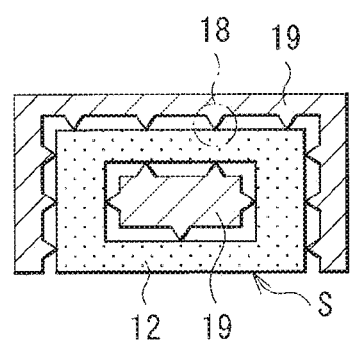

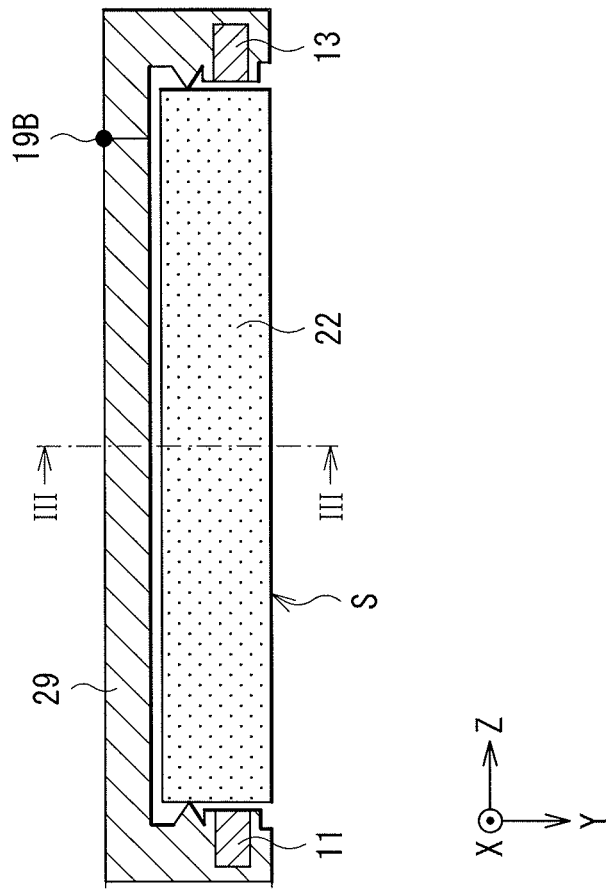
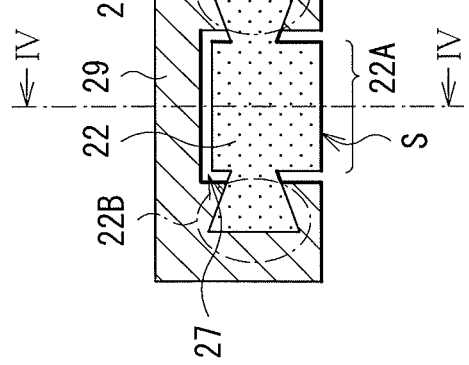

[ FIG. 11A ]
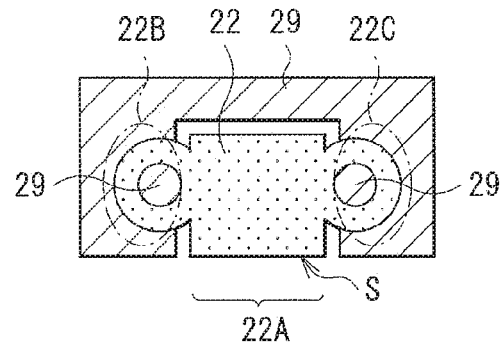
[ FIG. 11B ]
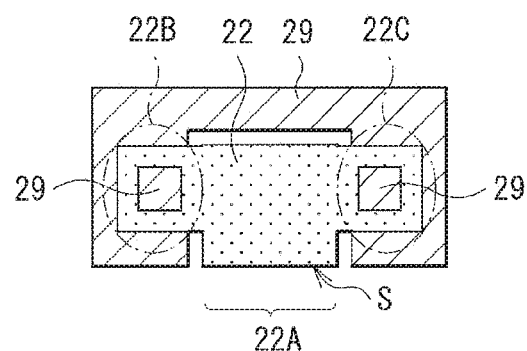
[ FIG. 11C ]
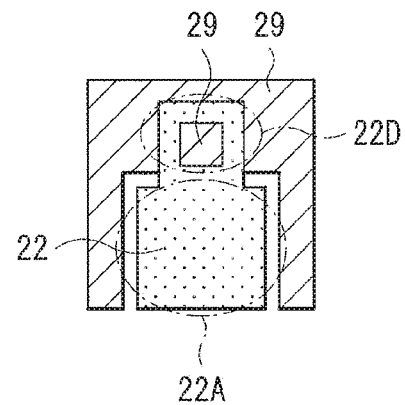

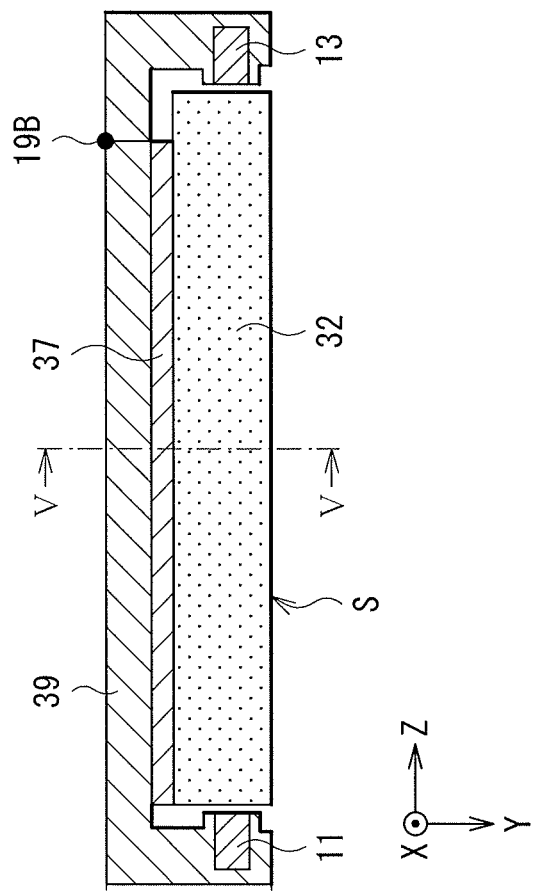

[ FIG. 13 ]
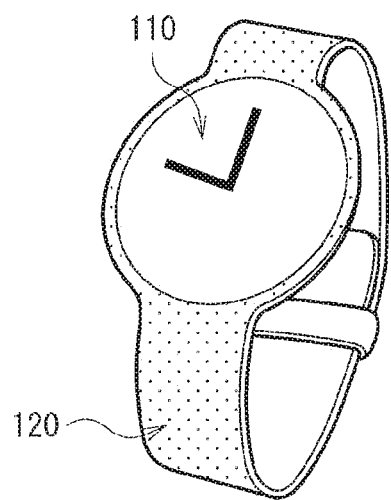
[ FIG. 14 ]
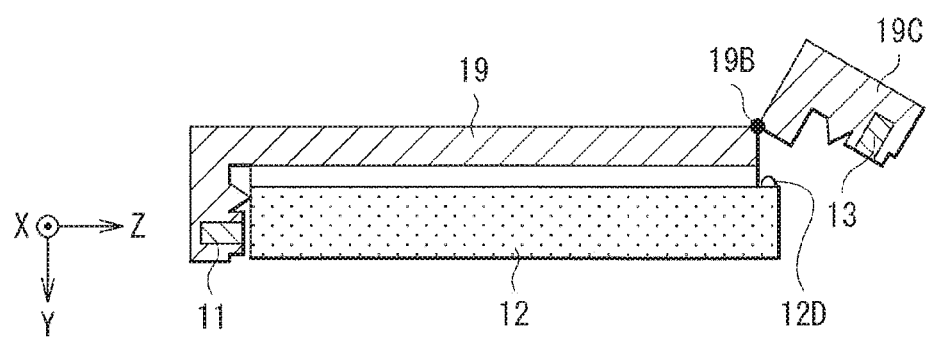

PULSE MEASURING DEVICE, PULSE MEASURING UNIT, AND ELECTRONIC APPARATUS

CROSS REFERENCE TO RELATED APPLICATIONS

This application is a U.S. National Phase of International Patent Application No. PCT/JP2016/083913 filed Nov. 16, 2016, which claims priority benefit of Japanese Patent Application No. JP 2015-238185 filed in the Japan Patent Office on Dec. 7, 2015. Each of the above-referenced applications is hereby incorporated herein by reference in its entirety.

TECHNICAL FIELD

The disclosure relates to a pulse measuring device and a pulse measuring unit used to measure pulses, and to an electronic apparatus including such a pulse measuring device.

BACKGROUND ART

A photoplethysmography (PPG: Photoplethysmography) method is one of pulse measuring techniques. This photoplethysmography method measures a change in the volume of a blood vessel using a light absorption property of hemoglobin in blood. For example, PTL 1 and PTL 2 each disclose a pulse measuring unit that guides, through a light guide body to a light-receiving device, light emitted from a light-emitting device. The pulse measuring unit generates pulse information on the basis of a change in an amount of light received in the light-receiving device when a human body is brought into contact with the light guide body.

CITATION LIST

Patent Literature

PTL 1: Japanese Unexamined Patent Application Publication No. 2012-176225
PTL 2: Japanese Unexamined Patent Application Publication No. 2015-93163

SUMMARY OF THE INVENTION

In general, it is desirable that a measuring unit have a high measurement accuracy. In the above-described PTL 1 and PTL 2, however, it is unknown as to how a light-emitting device, a light guide body, and a light-receiving device are disposed in a housing, and the measurement accuracy may possibly be reduced depending on their positions.

It is desirable to provide a pulse measuring device, a pulse measuring unit, and an electronic apparatus that are able to increase a measurement accuracy.

A pulse measuring device according to an embodiment of the disclosure includes a housing, a light-emitting device, a light-receiving device, and a light guide body. The light guide body has a first end surface facing the light-emitting device, a second end surface facing the first end surface and facing the light-receiving device, one or a plurality of first side surfaces covered by the housing, and one or a plurality of second side surfaces exposed from the housing.

A pulse measuring unit according to an embodiment of the disclosure includes a pulse measuring device and a signal processor. The pulse measuring device has a housing, a light-emitting device, a light-receiving device, and a light guide body. The light guide body includes a first end surface facing the light-emitting device, a second end surface facing the first end surface and facing the light-receiving device, one or a plurality of first side surfaces covered by the housing, and one or a plurality of second side surfaces exposed from the housing. The signal processor generates pulse information of a user on the basis of an amount of light received in the light-receiving device.

An electronic apparatus according to an embodiment of the disclosure includes a pulse measuring device, a signal processor, and a processor. The pulse measuring device has a housing, a light-emitting device, a light-receiving device, and a light guide body. The light guide body includes a first end surface facing the light-emitting device, a second end surface facing the first end surface and facing the light-receiving device, one or a plurality of first side surfaces covered by the housing, and one or a plurality of second side surfaces exposed from the housing. The signal processor generates pulse information of a user on the basis of an amount of light received in the light-receiving device. The processor performs, with the pulse information, a predetermined process.

In the pulse measuring device, the pulse measuring unit, and the electronic apparatus according to the respective embodiments of the disclosure, light emitted from the light-emitting device enters the light guide body via the first end surface. Further, light emitted via the second end surface of the light guide body is received by the light-receiving device. One or the plurality of first side surfaces of the light guide body is covered by the housing, and one or the plurality of second side surfaces is exposed from the housing.

According to the pulse measuring device, the pulse measuring unit, and the electronic apparatus of the respective embodiments of the disclosure, one or the plurality of first side surfaces of the light guide body is covered by the housing, and one or the plurality of second side surfaces is exposed from the housing. This makes it possible to increase a measurement accuracy. It is to be noted that effects described here are not necessarily limited and may include any of effects that are described herein.

BRIEF DESCRIPTION OF DRAWING

FIG. 1 is a block diagram that illustrates one configuration example of a pulse measuring unit according to an embodiment of the disclosure.

FIGS. 2A and 2B are cross-sectional views that illustrates one configuration example of a pulse measuring device according to a first embodiment.

FIG. 3 is an explanatory drawing that illustrates one operation example of the pulse measuring device illustrated in FIG. 1.

FIG. 4A is an explanatory drawing that illustrates one operation example of the pulse measuring device illustrated in FIG. 1.

FIG. 4B is an explanatory drawing that illustrates one operation example of the pulse measuring device illustrated in FIG. 1.

FIG. 5 is an explanatory drawing that illustrates one operation example of the pulse measuring device according to a modification example of the first embodiment.

FIG. 6 is an explanatory drawing that illustrates one operation example of the pulse measuring device according to a modification example of the first embodiment.

FIGS. 7A and 7B is a are cross-sectional views that illustrates one configuration example of the pulse measuring device according to a modification example of the first embodiment.

FIGS. 8A and 8B is a are cross-sectional views that illustrates one configuration example of the pulse measuring device according to a modification example of the first embodiment.

FIG. 9A is a cross-sectional view that illustrates one configuration example of the pulse measuring device according to a modification example of the first embodiment.

FIG. 9B is a cross-sectional view that illustrates one configuration example of the pulse measuring device according to a modification example of the first embodiment.

FIG. 9C is a cross-sectional view that illustrates one configuration example of the pulse measuring device according to a modification example of the first embodiment.

FIG. 9D is a cross-sectional view that illustrates one configuration example of the pulse measuring device according to a modification example of the first embodiment.

FIG. 9E is a cross-sectional view that illustrates one configuration example of the pulse measuring device according to a modification example of the first embodiment.

FIG. 9F is a cross-sectional view that illustrates one configuration example of the pulse measuring device according to a modification example of the first embodiment.

FIG. 9G is a cross-sectional view that illustrates one configuration example of the pulse measuring device according to a modification example of the first embodiment.

FIG. 9H is a cross-sectional view that illustrates one configuration example of the pulse measuring device according to a modification example of the first embodiment.

FIGS. 10A and 10B is a are cross-sectional views that illustrates one configuration example of a pulse measuring device according to a second embodiment.

FIG. 11A is a cross-sectional view that illustrates one configuration example of the pulse measuring device according to a modification example of the second embodiment.

FIG. 11B is a cross-sectional view that illustrates one configuration example of the pulse measuring device according to a modification example of the second embodiment.

FIG. 11C is a cross-sectional view that illustrates one configuration example of the pulse measuring device according to a modification example of the second embodiment.

FIGS. 12A and 12B is a are cross-sectional views that illustrates one configuration example of a pulse measuring device according to a third embodiment.

FIG. 13 is a perspective view that illustrates an external configuration of a watch to which an embodiment is applied.

FIG. 14 is a cross-sectional view that illustrates one configuration example of the pulse measuring device according to a modification example.

MODES FOR CARRYING OUT THE INVENTION

In the following, embodiments of the disclosure are described in detail with reference to the drawings. It is to be noted that description is made in the following order.

1. First Embodiment
2. Second Embodiment
3. Third Embodiment
4. Application Examples

1. First Embodiment

[Configuration]

FIG. 1 illustrates one configuration example of a pulse measuring unit (pulse measuring unit 1) according to a first embodiment. The pulse measuring unit 1 includes a pulse measuring device 10, a controller 8, and a signal processor 9.

The pulse measuring device 10 has a light-emitting device 11, a light guide body 12, and a light-receiving device 13. The light-emitting device 11 includes, for example, an LED (Light Emitting Diode), and emits light on the basis of control by the controller 8. A wavelength of the light may be a wavelength in a visible region or wavelength in a near-infrared or infrared region. The light guide body 12 includes, for example, an acrylic resin, and guides, to the light-receiving device 13, the light emitted from the light-emitting device 11. The light-receiving device 13 includes, for example, a PD (Photo Diode). The light-receiving device 13 receives the light guided by the light guide body 12, and provides, to the signal processor 9, a light receiving signal S1 corresponding to an amount of light received.

The signal processor 9 performs a predetermined signal process on the basis of the light receiving signal S1 provided from the light-receiving device 13 to thereby generate pulse information S2. The controller 8 provides control signals to the light-emitting device 11, the light-receiving device 13, and the signal processor 9 to thereby control an operation of the pulse measuring unit 1.

With this configuration, as described later, the pulse measuring unit 1 generates the pulse information S2 on the basis of a change in the amount of light received in the light-receiving device 13 when a human body is brought into contact with the light guide body 12.

FIGS. 2A and 2B illustrate one configuration example of the pulse measuring device 10. FIG. 2A illustrates a cross-sectional view of FIG. 2B taken along I-I in an arrow direction. FIG. 2B illustrates a cross-sectional view of FIG. 2A taken along II-II in an arrow direction.

The light guide body 12 has, in this example, an alphabet "T"-like cross-sectional shape within an XY plane and extends in a Z direction. As illustrated in FIG. 2B, the light-emitting device 11 is provided at a position facing one end surface 12A of the light guide body 12, and the light-receiving device 13 is provided at a position facing the other end surface 12B of the light guide body 12. This allows the light emitted from the light-emitting device 11 to enter the inside of the light guide body 12 from the end surface 12A of the light guide body 12, advance through the inside of the light guide body 12 to reach the end surface 12B, and be received by the light-receiving device 13.

The light-emitting device 11, the light guide body 12, and the light-receiving device 13 are contained in the housing 19. The housing 19 may include, for example, a metal, a plastic, etc. As illustrated in FIG. 2A, this housing 19 has, within the XY plane, a cavity that has a similar shape to the cross-sectional shape of the light guide body 12. This allows the light guide body 12 to be contained in such a way as to be in engagement with the housing 19. Of side surfaces of the light guide body 12 (surfaces intersecting the XY plane), a side surface S of the light guide body 12 is exposed and the other surfaces are covered by the housing 19, in the pulse measuring device 10. This enables the human body to come into contact with the side surface S of the light guide body 12.

In the housing 19, a surface facing the light guide body 12 is formed with a plurality of spacers 18. In this example, the plurality of spacers 18 are formed integrally with the housing 19. The spacers 18 each have a triangular cross-sectional shape within the XY plane and extend in the Z direction. The spacers 18 are each in contact with the light guide body 12 through small contact area. These spacers 18 form gaps 17 between the housing 19 and the light guide body 12. A refractive index of air in the gap 17 is lower than a refractive index of the light guide body 12. Thus, the pulse measuring device 10 allows a portion of the light emitted from the light-emitting device 11 to be totally reflected at an interface of the light guide body 12 upon advancing through the inside of the light guide body 12.

In addition, in this example, the pulse measuring device 10 allows a portion (an opening-closing part 19C) of the housing 19 to be opened and closed by a hinge 19B, as illustrated in FIG. 3. Further, when closed, the portion (the opening-closing part 19C) of the housing 19 is fixed to a main body of the housing 19 by an unillustrated fixing member, preventing the portion from opening easily. For such a fixing member, a fitting structure may be used in which a convex part provided on one side and a concave part provided on the other side come into mesh engagement, for example. Alternatively, the portion may be fixed with a screw so as not to open. The pulse measuring device 10 allows for a removal of the light guide body 12 by opening the opening-closing part 19C of the housing 19 and sliding the light guide body 12 in the Z direction. The pulse measuring device 10 thereby allows for a replacement of the light guide body 12 in a case where, for example, the side surface S of the light guide body 12 is tainted, the side surface S is scratched, or skin oil is attached to the side surface S. Consequently, the pulse measuring unit 1 makes it possible to increase a measurement accuracy.

[Operations and Workings]

Subsequently, description will be given on operations and workings of the pulse measuring unit 1 according to the embodiment.

[Outline of General Operation]

First, an outline of a general operation of the pulse measuring unit 1 will be described with reference with FIG. 1. The light-emitting device 11 emits the light on the basis of the control by the controller 8. The light guide body 12 guides, to the light-receiving device 13, the light emitted from the light-emitting device 11. The light-receiving device 13 receives the light guided by the light guide body 12 and provides, to the signal processor 9, the light receiving signal S1 corresponding to the amount of light received. The signal processor 9 performs the predetermined signal process on the basis of the light receiving signal S1 provided from the light-receiving device 13 to thereby generate the pulse information S2. The controller 8 controls the operation of the pulse measuring unit 1.

[Detailed Operation]

FIGS. 4A and 4B illustrate one operation example of the pulse measuring device 10. FIG. 4A illustrates a case where the human body is not in contact with the pulse measuring device 10, and FIG. 4B illustrates a case where the human body is in contact with the pulse measuring device 10. Here, light L1 and light L2 each advance in a direction that satisfies conditions of total reflection.

In this example, the light L1 emitted from the light-emitting device 11 advances through the inside of the light guide body 12 while being totally reflected at the interface. In a case where the human body is not in contact with the pulse measuring device 10 (FIG. 4A), the light L1 advances through the inside of the light guide body 12 while being totally reflected at the interface of the light guide body 12, and is received by the light-receiving device 13.

On the other hand, in a case where the human body is in contact with the pulse measuring device 10 (FIG. 4B), the light that advances through the inside of the light guide body 12 enters the human body HB via a contact surface ST. In other words, in a case where the human body HB is in contact with the light guide body 12 in this manner, the conditions of the total reflection are not satisfied at the contact surface ST, which makes the light enter the human body HB without being subjected to the total reflection. A portion of the light having entered the human body HB is absorbed by hemoglobin contained in blood flowing in capillaries of the human body HB. In addition, the portion of the light having entered the human body HB is scattered inside the human body HB. Then, a portion of light scattered enters the light guide body 12 again via the contact surface ST. A portion of the light having entered the light guide body 12 again (the light L2) advances through the inside of the light guide body 12 while being totally reflected at the interface of the light guide body 12, and is received by the light-receiving device 13. In this manner, the amount of light received by the light-receiving device 13 becomes an amount that corresponds to the volume of capillaries, owing to the absorption by the hemoglobin of the portion of the light having entered the human body HB. The light-receiving device 13 generates the light receiving signal S1 corresponding to the amount of light received. Further, the signal processor 9 performs the predetermined signal process on the basis of the light receiving signal S1 to thereby generate the pulse information S2. The pulse measuring unit 1 measures pulses in this manner.

In this manner, the pulse measuring unit 1 is provided with the housing 19 in which the side surface S of the light guide body 12 is exposed and which covers the other surfaces. Further, the pulse measuring unit 1 has the plurality of spacers 18, and forms the gaps 17 between the housing 19 and the light guide body 12. This enables the light L1 emitted from the light-emitting device 11 to be totally reflected at the side surfaces other than the side surface S upon advancing through the inside of the light guide body 12, and to be totally reflected in a region on the side surface S other than the contact surface ST. The pulse measuring unit 1 thereby allows the light emitted from the light-emitting device 11 and the light, having been scattered inside the human body HB and having entered the light guide body 12 again, to be guided effectively to the light-receiving device 13, which makes it possible to increase the measuring accuracy.

In addition, the pulse measuring unit 1 has a configuration in which the light guide body 12 comes into engagement with the housing 19. Specifically, the light guide body 12 has the alphabet "T"-like cross-sectional shape within the XY plane and the housing 19 has the same alphabet "T"-like cavity. This makes it possible to fix the light guide body 12 within the housing 19 while making it difficult to come off, with a simple configuration.

In addition, the pulse measuring unit 1 allows for the replacement of the light guide body 12. This allows for the replacement of the light guide body 12 in a case where, for example, the side surface S of the light guide body 12 is tainted, the side surface S is scratched, or skin oil is attached to the side surface S. Consequently, the pulse measuring unit 1 makes it possible to increase the measurement accuracy.

[Effects]

As described above, in this embodiment, the housing is provided that exposes the side surface S of the light guide body and covers the other surfaces, and the plurality of spacers are provided that form the gaps between the housing and the light guide body. Hence, it is possible to increase the measurement accuracy.

In this embodiment, the light guide body comes into engagement with the housing. This makes it possible to fix the light guide body within the housing while making it difficult to come off, with a simple configuration.

In this embodiment, the light guide body is replaceable. Hence, it is possible to increase the measurement accuracy.

Modification Example 1-1

In the above-described embodiment, the light guide body 12 and the housing 19 may include an elastomeric resin. As illustrated in FIG. 5, this enables the pulse measuring device 10 to be curved in accordance with a contact part of the human body, and thereby makes it possible to increase the contact area. As a result, it is possible to perform a measurement of pulses through contacting with various parts of the human body such as an arm, a leg, or a neck. Such a light guide body 12 may include a resin such as a silicon resin or an arton resin. In addition, such a housing 19 may include a resin such as a urethane resin or a flexible epoxy resin.

Modification Example 1-2

In the above-described embodiment, the hinge 19B is provided to allow the portion (the opening-closing part 19C) of the housing 19 to be opened and closed; however, it is not limited thereto. For example, the portion (the opening-closing part 19C) and the main body of the housing 19 may be separable without providing the hinge 19B. Further, as illustrated in FIG. 6, the main body of the housing 19 and the portion (the opening-closing part 19C) may be coupled by a coupling member 19D that includes a soft material, for example. In this example, the housing 19 has a hole for containing the coupling member 19D. Further, in a case where the main body of the housing 19 and the portion (the opening-closing part 19C) are coupled together, this coupling member 19D is contained in the hole provided in the housing 19.

Modification Example 1-3

In the above-described embodiment, the spacers 18 each have the triangular cross-sectional shape within the XY plane and extend in the Z direction; however, it is not limited thereto. As illustrated in FIGS. 7A and 7B, conical-shaped spacers 18 may be used, for example. In this example, the spacers 18 are randomly disposed in the Z direction. Note that this is non-limiting, and the spacers 18 may be disposed at regular intervals in the Z direction. In addition, as illustrated in FIGS. 8A and 8B, hemisphere-shaped spacers 18 may be used, for example.

Modification Example 1-4

In the above-described embodiment, the light guide body 12 has the alphabet "T"-like cross-sectional shape within the XY plane; however, it is not limited thereto. As illustrated in FIG. 9A, the light guide body 12 may have a trapezoidal cross-sectional shape, for example. The lower side of this trapezoid corresponds to the side surface S, and a length of the lower side is shorter than the length of the upper side. The housing 19 has a cavity that has a similar shape to the cross-sectional shape of the light guide body 12. The light guide body 12 is housed in such a way as to be in engagement with the housing 19. Even with this configuration, it is possible to fix the light guide body 12 within the housing 19 while making it difficult to come off.

Similarly, as illustrated in FIG. 9B, the light guide body 12 may have, within the XY plane, such a cross-sectional shape in which a portion of a circle is cut off, for example. The cut-off portion of this circle corresponds to the side surface S. In addition, as illustrated in FIG. 9C, the light guide body 12 may have a cross-sectional shape having a shape in which a plurality of rectangles are combined, for example. The lower side of this shape corresponds to the side surface S, and a length of the lower side is shorter than the length of the upper side. In addition, as illustrated in FIG. 9D, the light guide body 12 may have a hexagonal cross-sectional shape, for example. One side of this hexagon corresponds to the side surface S. In addition, as illustrated in FIG. 9E, the light guide body 12 may have a cross-shaped cross-sectional shape, for example. A portion of this cross shape corresponds to the side surface S.

In addition, as illustrated in FIG. 9F, the light guide body 12 may have such a cross-sectional shape in which corners of an alphabet "U" is sharpened, for example. A portion of the housing 19 is disposed on inner side of the letter "U", thereby allowing the light guide body 12 to be engaged with the housing 19. In this example, two portions on both ends of the letter "U" correspond to the side surface S. In addition, as illustrated in FIG. 9G, the light guide body 12 may have a semi-arc-like cross-sectional shape, for example. A portion of the housing 19 is disposed on inner side of the semi-arc, thereby allowing the light guide body 12 to be engaged with the housing 19. In this example, two portions on both ends of the semi-arc correspond to the side surface S. In addition, as illustrated in FIG. 9H, the light guide body 12 may have a square cross-sectional shape in which a hollow region is provided in the middle, for example. The housing 19 is disposed on inner side of the hollow region, thereby allowing the light guide body 12 to be engaged with the housing 19. In this example, the lower side of the square corresponds to the side surface S.

Other Modification Example

In addition, two or more of the modification examples may be combined.

2. Second Embodiment

Next, a pulse measuring unit 2 according to a second embodiment is described. In this embodiment, a method of providing the gaps 17 is different from that in the first embodiment. In other words, in the above-described first embodiment (FIGS. 2A and 2B), the gaps 17 are provided using the spacers 18. In place of this, in this embodiment, the gaps are provided without using the spacers 18. It is to be noted that substantially like components are denoted by like numerals as of the pulse measuring unit 1 according to the above-described first embodiment and will not be further described.

FIGS. 10A and 10B illustrate one configuration example of a pulse measuring device 20 of the pulse measuring unit 2. FIG. 10A illustrates a cross-sectional view of FIG. 10B taken along III-III in an arrow direction, and FIG. 10B illustrates a cross-sectional view of FIG. 10A taken along IV-IV in an arrow direction. The pulse measuring device 20 has the light-emitting device 11, a light guide body 22, and the light-receiving device 13. The light-emitting device 11, the light guide body 22, and the light-receiving device 13 are contained in a housing 29.

The light guide body 22 has a main body 22A and supporting sections 22B and 22C. The main body 22A has a square cross-sectional shape within the XY plane, and the supporting sections 22B and 22C each have a trapezoidal cross-sectional shape. As illustrated in FIG. 10A, the supporting sections 22B and 22C are disposed on the right and left sides of the main body 22A. The supporting sections 22B and 22C are in contact with an inner surface of the housing 29. In this manner, in the pulse measuring device 20, the light guide body 22 is supported by the supporting sections 22B and 22C that are in contact with the inner surface of the housing 29. Consequently, gaps 27 are formed between the main body 22A and the housing 29.

In this manner, the pulse measuring unit 2 is provided with the supporting sections 22B and 22C that are in contact with the inner surface of the housing 29 to thereby support the light guide body 22. In particular, unlike the light guide body 12 according to the above-described first embodiment, the main body 22A includes no spacer, making it possible to effectively guide the light to the light-receiving device 13 by the total reflection and thereby to increase the measurement accuracy.

As described above, in the embodiment, the supporting sections are provided that are in contact with the inner surface of the housing to thereby support the light guide body. Hence, it is possible to increase the measurement accuracy.

Modification Example 2-1

In the above-described embodiment, the supporting sections 22B and 22C each have the trapezoidal cross-sectional shape within the XY plane; however, it is not limited thereto. In place of this, as illustrated in FIG. 11A, the supporting sections 22B and 22C each may have such a cross-sectional shape in which a portion of a circular shape is cut off. In this example, the supporting sections 22B and 22C each have a hollow region, and a portion of the housing 29 is disposed in the hollow region. In addition, as illustrated in FIG. 11B, the supporting sections 22B and 22C each may have a square cross-sectional shape. In this example as well, the supporting sections 22B and 22C each also have the hollow region, and a portion of the housing 29 is disposed in the hollow region. It is noted that this is non-limiting, and the supporting sections 22B and 22C may not have the hollow regions. In addition, in these examples, the two supporting sections 22B and 22C are provided on the left and right sides of the main body 22A. However, this is non-limiting and one supporting section 22D may be provided alternatively as illustrated in FIG. 11C. In this example, the supporting section 22D is provided on the upper side of the main body 22A. However, this is non-limiting and alternatively, the supporting section 22D may be provided on the left side of the main body 22A, or may be provided on the right side of the main body 22A.

3. Third Embodiment

Next, a pulse measuring unit 3 according to a third embodiment is described. In this embodiment, an optical member having a refractive index lower than a refractive index of the light guide body is disposed between the light guide body and the housing. It is to be noted that substantially like components are denoted by like numerals as of the pulse measuring unit 1 according to the above-described first embodiment and will not be further described.

FIGS. 12A and 12B illustrate one configuration example of a pulse measuring device 30 of the pulse measuring unit 3. FIG. 12A illustrates a cross-sectional view of FIG. 12B taken along V-V in an arrow direction, and FIG. 12B illustrates a cross-sectional view of FIG. 12A taken along VI-VI in an arrow direction. The pulse measuring device 30 has the light-emitting device 11, a light guide body 32, and the light-receiving device 13. The light-emitting device 11, the light guide body 32, and the light-receiving device 13 are contained in a housing 39.

An optical member 37 is provided between the light guide body 32 and the housing 39. The optical member 37 has a refractive index lower than a refractive index of the light guide body 32. In a case where the light guide body 32 includes an acrylic resin with a refractive index of 1.49, for example, the optical member 37 may include a fluororesin with a refractive index of 1.34. This enables the light emitted from the light-emitting device 11 to be totally reflected at an interface of the light guide body 32 when the light advances through the inside of the light guide body 32.

In this manner, in the pulse measuring unit 3, the optical member 37 having the refractive index lower than the refractive index of the light guide body 32 is disposed between the light guide body 32 and an inner surface of the housing 39. In particular, unlike the light guide body 12 according to the above-described first embodiment, the pulse measuring unit 3 has no spacer, making it possible to effectively guide the light to the light-receiving device 13 by the total reflection and thereby to increase the measurement accuracy.

As described above, in this embodiment, the optical member having the refractive index lower than the refractive index of the light guide body is provided between the light guide body and the inner surface of the housing. Hence, it is possible to increase the measurement accuracy.

4. Application Examples

Next, description is given of application examples of the pulse measuring unit described in the above-described embodiments and modification examples.

FIG. 13 illustrates an external appearance of a watch to which the pulse measuring unit according to any of the above embodiments, etc. is applied. This watch has a face 110 and a band 120, for example. The pulse measuring unit according to any of the above embodiments, etc., is mounted on a surface which is located on the back side surface of the face 110 and which comes into contact with an arm of a user.

It is possible to apply the pulse measuring unit according to any of the above embodiments, etc., to a variety of objects to be worn by the user, such as a wristband, glasses, or a ring, besides the watch as described above. This makes it possible to configure a wearable terminal that is able to measure pulses.

Although the technology has been described by giving some embodiments and their modification examples, their specific adaptations, and applications to an electronic apparatus, the technology is not limited to these embodiments, etc. and may be modified in a variety of ways.

For example, in each of the embodiments described above, the light guide body is replaceable. In this case, as illustrated in FIG. 14, the light guide body 12 may be provided with a projection 12D to allow the light guide body 12 to be pulled out easily from the housing 19. It is noted that, in this example, the modification example is applied to the pulse measuring device 10 according to the first embodiment, but also may be applied to the pulse measuring device 20 according to the second embodiment and the pulse measuring device 30 according to the third embodiment.

Note that effects described herein are merely illustrative and non-limiting, and effects other than those described herein may also be achieved.

Note that the technology may achieve the following configurations.

(1)
A pulse measuring device including:
a housing;
a light-emitting device;
a light-receiving device; and
a light guide body having a first end surface facing the light-emitting device, a second end surface facing the first end surface and facing the light-receiving device, one or a plurality of first side surfaces covered by the housing, and one or a plurality of second side surfaces exposed from the housing.

(2)
The pulse measuring device according to (1), in which a shape, of an inner surface of the housing, facing the one or the plurality of first side surfaces corresponds to a shape of the one or the plurality of first side surfaces.

(3)
The pulse measuring device according to (2), in which
the light guide body extends in an extending direction from the first end surface to the second end surface, and
a width of the light guide body which is in a direction intersecting the extending direction and which is at a position away from the one or the plurality of second side surfaces by a first distance is smaller than a width of the light guide body which is in the direction intersecting the extending direction and which is at a position away from the one or the plurality of second side surfaces by a second distance, the second distance being larger than the first distance.

(4)
The pulse measuring device according to any one of (1) to (3), in which the one or the plurality of first side surfaces includes a third side surface that is spaced away from an inner surface of the housing.

(5)
The pulse measuring device according to (4), in which a gap is provided between the third side surface and the inner surface of the housing.

(6)
The pulse measuring device according to (5), further including one or a plurality of spacers provided between the third side surface and the inner surface of the housing.

(7)
The pulse measuring device according to (5), in which the one or the plurality of first side surfaces includes a fourth side surface that is in contact with the inner surface of the housing.

(8)
The pulse measuring device according to (4), further including an optical member provided between the third side surface and the inner surface of the housing, and having a refractive index smaller than a refractive index of the light guide body.

(9)
The pulse measuring device according to any one of (1) to (8), in which the housing allows the light guide body to be slidable in a predetermined direction within a plane of the one or the plurality of second side surfaces.

(10)
The pulse measuring device according to any one of (1) to (9), in which the light guide body and the housing include an elastomeric resin.

(11)
The pulse measuring device according to any one of (1) to (10), in which the light-emitting device and the light-receiving device are fixed inside the housing.

(12)
A pulse measuring unit including:
a pulse measuring device, the pulse measuring device including
a housing,
a light-emitting device,
a light-receiving device, and
a light guide body having a first end surface facing the light-emitting device, a second end surface facing the first end surface and facing the light-receiving device, one or a plurality of first side surfaces covered by the housing, and one or a plurality of second side surfaces exposed from the housing; and
a signal processor that generates pulse information of a user on a basis of an amount of light received in the light-receiving device.

(13)
An electronic apparatus including:
a pulse measuring device, the pulse measuring device including
a housing,
a light-emitting device,
a light-receiving device, and
a light guide body having a first end surface facing the light-emitting device, a second end surface facing the first end surface and facing the light-receiving device, one or a plurality of first side surfaces covered by the housing, and one or a plurality of second side surfaces exposed from the housing;
a signal processor that generates pulse information of a user on a basis of an amount of light received in the light-receiving device; and
a processor that performs, with the pulse information, a predetermined process.

This application claims the benefit of Japanese Priority Patent Application JP2015-238185 filed with the Japan Patent Office on Dec. 7, 2015, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:
1. A pulse measuring device, comprising:
a housing;
a light-emitting device;
a light-receiving device; and
a light guide body including:
a first end surface that faces the light-emitting device;
a second end surface that faces the first end surface and the light-receiving device;
at least one first side surface covered by the housing; and at least one second side surface exposed from the housing, wherein
a shape of an inner surface of the housing corresponds to a shape of the at least one first side surface,
the inner surface of the housing faces the at least one first side surface,
the light guide body extends in an extending direction from the first end surface to the second end surface,
a first width of the light guide body and a second width of the light guide body are in a direction that intersects the extending direction,
the first width of the light guide body is at a first position away from the at least one second side surface by a first distance,
the second width of the light guide body is at a second position away from the at least one second side surface by a second distance,
the first width of the light guide body is smaller than the second width of the light guide body, and
the second distance is larger than the first distance.

2. The pulse measuring device according to claim 1, wherein
the light guide body further includes a third side surface that is spaced away from the inner surface of the housing.

3. The pulse measuring device according to claim 2, wherein
a gap is between the third side surface and the inner surface of the housing.

4. The pulse measuring device according to claim 3, further comprising at least one spacer between the third side surface and the inner surface of the housing.

5. The pulse measuring device according to claim 3, wherein
the light guide body further includes a fourth side surface that is in contact with the inner surface of the housing.

6. The pulse measuring device according to claim 2, further comprising an optical member between the third side surface and the inner surface of the housing, wherein
a refractive index of the optical member is smaller than a refractive index of the light guide body.

7. The pulse measuring device according to claim 1, wherein
the light guide body is slidable in the housing in a specific direction within a plane of the at least one second side surface.

8. The pulse measuring device according to claim 1, wherein the light guide body and the housing include an elastomeric resin.

9. The pulse measuring device according to claim 1, wherein the light-emitting device and the light-receiving device are fixed inside the housing.

10. A pulse measuring unit, comprising:
a pulse measuring device that includes:
a housing;
a light-emitting device;
a light-receiving device configured to receive an amount of light; and
a light guide body including:
a first end surface that faces the light-emitting device;
a second end surface that faces the first end surface and the light-receiving device;
at least one first side surface covered by the housing; and
at least one second side surface exposed from the housing, wherein
a shape of an inner surface of the housing corresponds to a shape of the at least one first side surface,
the inner surface of the housing faces the at least one first side surface,
the light guide body extends in an extending direction from the first end surface to the second end surface,
a first width of the light guide body and a second width of the light guide body are in a direction that intersects the extending direction,
the first width of the light guide body is at a first position away from the at least one second side surface by a first distance,
the second width of the light guide body is at a second position away from the at least one second side surface by a second distance,
the first width of the light guide body is smaller than the second width of the light guide body, and
the second distance is larger than the first distance; and
a signal processor configured to generate pulse information of a user based on the amount of light received by the light-receiving device.

11. An electronic apparatus, comprising:
a pulse measuring device that includes:
a housing;
a light-emitting device;
a light-receiving device configured to receive an amount of light; and
a light guide body including:
a first end surface that faces the light-emitting device;
a second end surface that faces the first end surface and the light-receiving device;
at least one first side surface covered by the housing; and
at least one second side surface exposed from the housing, wherein
a shape of an inner surface of the housing corresponds to a shape of the at least one first side surface,
the inner surface of the housing faces the at least one first side surface,
the light guide body extends in an extending direction from the first end surface to the second end surface,
a first width of the light guide body and a second width of the light guide body are in a direction that intersects the extending direction,
the first width of the light guide body is at a first position away from the at least one second side surface by a first distance,
the second width of the light guide body is at a second position away from the at least one second side surface by a second distance, the first width of the light guide body is smaller than the second width of the light guide body, and
the second distance is larger than the first distance;
a signal processor configured to generate pulse information of a user based on the amount of light received the light-receiving device; and
a processor configured to perform a specific process based on the pulse information.

\* \* \* \* \*